United States Patent [19]

Ochoa et al.

[11] Patent Number: 5,443,983
[45] Date of Patent: Aug. 22, 1995

[54] METHOD OF CULTURING LYMPHOCYTES AND METHOD OF TREATMENT USING SUCH LYMPHOCYTES

[75] Inventors: Augusto C. Ochoa, St. Paul; Fritz H. Bach, Minneapolis; Barbara Alter, Marine on St. Croix, all of Minn.; Paul Sondel, Madison, Wis.

[73] Assignee: Regents of the University of Minnesota, Minneapolis, Minn.

[21] Appl. No.: 170,755

[22] Filed: Mar. 21, 1988

Related U.S. Application Data

[63] Continuation-in-part of Ser. No. 895,042, Aug. 8, 1986, abandoned.

[51] Int. Cl.$^6$ .................... C12N 5/02; C12N 5/08
[52] U.S. Cl. .................... 435/240.2; 435/2; 435/240.25
[58] Field of Search ............. 435/240.1, 240.2, 240.21, 435/240.25, 240.3, 240.31, 172.2, 240.26, 240.27; 935/108

[56] References Cited

U.S. PATENT DOCUMENTS

| | | | |
|---|---|---|---|
| 4,464,355 | 8/1984 | Fabricius et al. ............ | 424/101 |
| 4,518,584 | 5/1985 | Mark et al. . | |
| 4,604,377 | 8/1986 | Fernandes et al. . | |
| 4,636,463 | 1/1987 | Altman et al. ............. | 435/7 |
| 4,683,199 | 7/1987 | Palladino . | |
| 4,689,222 | 8/1987 | McMichael ................ | 424/88 |
| 4,690,915 | 9/1987 | Rosenberg ................. | 514/2 |
| 4,808,151 | 2/1989 | Dunn, Jr. et al. ............ | 604/6 |
| 4,908,433 | 3/1990 | Mertelsmann et al. . | |

FOREIGN PATENT DOCUMENTS

| | | |
|---|---|---|
| 0049611 | 4/1982 | European Pat. Off. . |
| 0203403 | 12/1986 | European Pat. Off. . |
| WO85/03948 | 9/1985 | WIPO . |
| WO88/00970 | 2/1988 | WIPO . |

OTHER PUBLICATIONS

P. M. Anderson et al., *Cancer Immunol. Immunother.*, 1988, 27, 82.
N. Berinstein et al., *J. Immunol.*, 1988, 140, 2839.
R. I. Fisher et al., *Ann. Int. Med.*, 1988, 108, 518.
T. D. Geppert et al., *J. Clin. Invest.*, 1988, 81, 1497.
S. Gillis et al., *J. Immunol.*, 1978, 120, 2027.
E. A. Grimm et al., *J. Exp. Med.*, 1983, 158, 1356.
E. A. Grimm et al., *J. Exp. Med.*, 1982, 155, 1823.
E. M. Janis et al., *Science*, 1989, 244, 713E.
O. Leo et al., *Proc. Natl. Acad. Sci. USA*, 1987, 84, 1374.
M. Malkovsky et al., *Nature*, 1987, 325, 262.
S. C. Meuer et al., *Proc. Natl. Acad. Sci. USA*, 1984, 81, 1509.
J. J. Mule et al., *Science*, 1984, 225, 1487.
L. M. Muul et al., *J. Immunol.*, 1987, 138, 989.
S. A. Rosenberg et al., *Ann. Int. Med.*, 1988, 108, 853.
S. A. Rosenberg et al., *Ann. of Surg.*, 1988, 208, 121.
K. A. Smith, *Science*, 1988, 240, 1169.
J. Stankova et al., *FASEB*, 1988, 2, Abstract No. 2114, 72nd Annual Meeting of FASEB, May 1988 (Meeting Abstract).
J. Stankova et al., *Cell. Immunol.*, 1989, 121, 13.
M. C. Turco et al., *Blood*, 1989, 74, 1651.
J. M. Zarling et al., *Nature*, 1978, 274, 269.

(List continued on next page.)

*Primary Examiner*—George C. Elliott
*Attorney, Agent, or Firm*—Foley & Lardner

[57] ABSTRACT

In accordance with the present invention, a method of culturing lymphocytes is disclosed in which the lymphocytes are cultured in the presence of interleukin-2 (IL-2) and an antibody to a lymphocyte surface receptor, preferably an antibody to a lymphocyte T3 surface receptor. Preferably, the antibody is monoclonal. Cells cultured with anti-CD3 maintain their LAK activity as they increase in number. The cells can also be cultured in the presence of an additional lymphokine to obtain additional LAK activity.

Methods of medical treatment are also disclosed in which cells cultured in accordance with the culturing methods of the present invention are introduced into the individual to be treated.

8 Claims, 5 Drawing Sheets

OTHER PUBLICATIONS

Ferrini et al. (1987), "Phenotypic and Functional Characterization of Recombinant Interleukin 2 (rIL-2)-Induced Activated Killer Cells: Analysis at the Population and Clonal Levels," *J. Immunol.* 138:1297.

Tatake et al. (1987), "Activation of Autoreactive Cytolytic T Lymphocyte Clone Against Human Melanoma by Anti-T3 Monoclonal Antibody and Autologous Accessory Cells," *Cell. Immunol.* 108:42.

Tsoukas, et al.; Journal of Immunology, vol. 135, No. 3, pp. 1719-1723; Sep. 1985.

Hogan, et al.; Journal of Immunology, vol. 135, No. 3, pp. 1731-1738; Sep. 1985.

Ochoa, et al.; The Journal of Immunology, vol. 138, No. 8, pp. 2728-2733; Apr. 15, 1987.

Van Wauwe, et al.; The Journal of Immunology, vol. 133, No. 1, pp. 129-132; Jul. 1, 1984.

Grimm et al, "Lymphokine-activated Killer Cell Phenomenon", J. of Experimental Medicine, vol. 157, pp. 884-897, Mar. 1983.

J. Fujito et al., *Eur. J. Cancer Clin. Oncol.*, 22, 445 (1986).

T. D. Geppert et al., *J. Clin. Invest.*, 81, 1497 (1988).

E. A. Grimm et al., *J. Exp. Med.*, 155, 1823 (1982).

M. L. Lotze et al., *Cancer Res.*, 41, 4420 (1981).

M. T. Lotze et al., *J. Surg. Res.*, 42, 580 (1987).

E. Lotzova et al., *Nat. Immun. Cell Growth Regul.*, 6, 219 (1987).

S. A. Rosenberg et al., *N. Engl. J. Med.*, 313, 1485 (1985).

S. Rosenberg, *J.N.C.I.*, 75, 595 (1985).

S. A. Rosenberg et al., *N. Engl. J. Med.*, 316, 889 (1987).

S. A. Rosenberg, in *Important Advances in Oncology*, V. T. DeVita et al., eds., J. P. Lippincott Co., Philadelphia, Pa. (1988) at pp. 217-257.

R. R. Salup et al., *Cancer Immunol. Immunother.*, 22, 31 (1986).

P. M. Sondel et al., *J. Immunol.*, 137, 502 (1986).

V. von Fliedner et al., *Progress in Chemical and Biological Research: Cellular Immunotherapy of Cancer*, 244, 223 (1987).

W. H. West et al., *J. Immunol.*, 118, 355 (1977).

S. C. Yang et al., *Proc. Annu. Meet. Am. Assoc. Cancer Res.*, 29 (1988), Abstract No. A1603 (Meeting Abstract).

Y. P. Yen et al., *Proc. Annu. Meet. Am. Assoc. Cancer Res.*, 28 (1987), Abstract No. 403 (Meeting Abstract).

Y. P. Yen et al., *Proc. Annu. Meet. Am. Assoc. Cancer Res.*, 29 (1988), Abstract No. A1616 (Meeting Abstract).

J. M. Zarling et al., *Cancer Immunol. Immunother.*, 15, 237 (1983).

Rabinowich et al. Cancer Research 47: 173-77 (1987).

Fujita et al. (1986).

Shu et al. J. Immunol. 136: 3891-98 (1986).

Muul et al. J. Immunol Meth. 88: 265-75 (1986).

Froelich et al. J. Immunol. Meth. 86: 205-11 (1986).

Brunda et al. Immunochemistry 105: 22776w (1986).

Itoh et al. J. Immunol. 136: 3910-15 (1986).

Whiteside et al. Int. J. Cancer 37: 803-11 (1986).

Miescher et al. J. Immunol. 136: 1899-907 (1986).

Rosenberg et al. Science 233: 1318-21 (1986).

Schwab et al. J. Immunol. 135: 1714-18 (1985).

Williams et al. J. Immunol. 135: 2249-55 (1985).

Brooks et al. J. Immunol. 135: 1145-52 (1985).

Shu et al. J. Immunol. 135: 2895-903 (1985).

Itoh et al. J. Immunol. 134: 3124-29 (1985).

Weiss et al. J. Clin. Immunol. 4: 165-71 (1984).

Grimm et al. Biological Abstracts 77: 60875 (1984).

Vose Int. J. Cancer 30: 135-42 (1982).

Fabricius et al. Immunobiol. 156: 364-71 (1979).

Strausser et al. J. Immunol. 121: 1491-95 (1978).

Rosenberg et al. J. Immunol. 121: 1951-55 (1978).

Ortaldo et al. Biological Abstracts 76: 58463 (1977).

Rosenberg et al. Adv. Cancer Res. 25: 323-88 (1977).

Frenster et al. "Immunotherapy of Human Neoplasms with Autologous Lymphocytes Activated In-Vitro," Proc. 5th Leukocyte Culture Conference, Harris ed. (1970).

METHOD OF CULTURING LYMPHOCYTES AND METHOD OF TREATMENT USING SUCH LYMPHOCYTES

This application is a continuation-in-part of application Ser. No. 895,042, filed Aug. 8, 1986.

FIELD OF THE INVENTION

The present invention relates to in vitro culturing of lymphocytes so as to illicit lytic "killer" or "lymphokine-activated killer (LAK)" activity in the lymphocyte population and treatment of tumor and other conditions, including acquired immunodeficiency syndrome (AIDS), with lymphocytes cultured according to the method of the present invention.

BACKGROUND OF THE INVENTION

Medical history is replete with attempts to manipulate the immune system with chemical, biochemical and cellular means. Many experimental protocols have been tried in which agents thought to enhance and/or increase the body's immune response to disease, including cancer, have been given to patients. Most of these trials have not been successful and in the few cases in which success has been reported it has been difficult to reproduce the successful aspects of the trial.

One of these experimental treatment protocols, known as "adoptive immunotherapy" or "cellular adoptive immunotherapy", involves the administration of immunologically active (immunocompetent) cells to an individual for the purpose of providing a beneficial immunological effect to the individual (e.g., reduction or control of cancerous or diseased tissue). These immunocompetent cells can be taken by venipuncture or leukopheresis either from the individual to be treated (autologous treatment) or from another individual (allogeneic treatment). The lymphocytes are cultured to increase their number and activate their antitumor activity and are then infused back into the patient. Animal experiments transferring immunocompetent cells from healthy animals to animals with cancerous tumors have suggested that adoptive immunotherapy can illicit an anti-tumor effect in certain tumor models with a high degree of effectiveness.

Samples of fresh (i.e., untreated) peripheral blood lymphocytes ("PBL"), a subclass of lymphocytes, are capable of lysing certain established tumor lines (e.g., K562) without any activation or treatment in the laboratory. West et al., J. Immunol. 118:355 (1977). Cells that can lyse these established tumor lines, including K562, have been designated natural killer ("NK") cells.

Populations of fresh PBL that have NK activity are, however, unable to lyse tumor lines such as Daudi, HL60 or fresh tumor targets (each being referred to herein as "NK resistant" targets). Human PBL cultured with interleukin-2 (IL-2) for as little as 3–5 days will develop the ability to lyse NK-resistant targets. Grimm et al., J. Exp. Med. 155:1823 (1982); Sondel et al., J. Immunol 137:502 (1986); Zarling et al., Cancer Immunol. Immunother. 15:237 (1983); Lotze et al., Cancer Res. 41:4420 (1981). As used throughout this specification and the appended claims "IL-2" shall include (1) naturally-derived interleukin-2, (2) recombinant interleukin-2, (3) interleukin-2 from any other source, and (4) peptides [e.g., fragments, homologs and analogs] which have the same biological activity as interleukin-2 for stimulating LAK activity regardless of the source of such peptides. Cells that have acquired the ability to lyse NK resistant targets after culturing with IL-2 have been designated lymphokine-activated killer ("LAK") cells. LAK activity and NK activity are currently distinguished by the ability of LAK cells to destroy NK-resistant targets.

Rosenberg et al. have obtained encouraging results in a significant number of patients, especially those with renal cell carcinoma, melanoma, tumors of the colon and non-Hodgkin lymphoma, using a treatment protocol combining the administration of LAK cells with the systemic administration of IL-2. Rosenberg, JNCI 75:595 (1985); Shu and Nisenkig, J. Immunol 135:2895 (1985); Rosenberg et al., N. Engl. J. Med. 313:1485 (1985). The IL-2 is administered systemically in an attempt to maintain LAK activity and to activate LAK activity in uncultured cells in the bloodstream. The effectiveness of the Rosenberg treatment protocol has been severely crippled, however, by the inability of the culturing methods of Rosenberg et al. to sufficiently increase LAK cell numbers in culture and to maintain LAK activity in cultured cells for more than five days. Rosenberg, supra; Shu and Nisenkig, supra; Rosenberg et al., supra; Muul et al., J. Immunol. Metth 88:265 (1986). LAK activity in cells cultured according to the Rosenberg method is short-lived and declines rapidly after day 5 of culture.

Rosenberg has suggested that approximately $2 \times 10^{10}$ to $2 \times 10^{11}$ cells with adequate LAK activity are required to achieve a therapeutic response. Since a typical sample of PBLs contains only $1-4 \times 10^9$ cells which can be activated to become LAK cells and the percentage of the cells originally taken from the lymphocyte source which, after activation and culturing by the Rosenberg method, are available for therapy has frequently been less than 100% (i.e., the number of activated cells available for infusion is less than the number of cells with which the activating culture was started), such high cell numbers can only be achieved through multiple leukopheresis and multiple LAK cell infusions which can be very hard on the health of a patient who is already severely compromised. This has made LAK cell adoptive immunotherapy a difficult, costly and medically troublesome task.

The Rosenberg treatment protocol has also been questioned due to the toxicity of systemically-administered IL-2. Some critics have proposed that many undesirable side effects, including accumulation of fluids in the lungs, fever, chills, decrease in urinary output, increase in creative and BUN levels, hyponatermia and death (in two reported cases), are the result of IL-2 administered in connection with LAK cell therapy. Rosenberg et al., N. Engl J. Med. 313(23):1485; Rosenberg et al., N, Engl. J. Med. 316(15):889. Elimination of these side effects by eliminating the need to administer IL-2 with the LAK cells would make LAK cell therapy a more tolerable and efficacious treatment.

It would therefore be desirable to provide a method for culturing lymphocytes that can produce the large number of activated cells necessary for practical and successful adoptive immunotherapy without the need to extract multiple samples of cells from a patient. It would also be desirable to provide a method for adoptive immunotherapy that does not require multiple leukopheresis or venipunctures or where the systemic administration of high doses of IL-2 can be attenuated or eliminated while still achieving anti-tumor effects.

SUMMARY OF THE INVENTION

In accordance with the present invention, a method of culturing lymphocytes is disclosed in which the lymphocytes are cultured in the presence of interleukin-2 (IL-2) and an antibody to a lymphocyte surface receptor, preferably an antibody to a lymphocyte T3 surface receptor (e.g., anti-CD3). Preferably, the antibody is monoclonal. Cells cultured with anti-CD3 develop and maintain LAK activity as they increase in number. Preferably, the cells are cultured in the presence of IL-2 and the surface receptor antibody during the first 48 hours of culture; however, the present invention is intended to encompass any protocol for culturing lymphocytes in which the lymphocytes are in the presence of both IL-2 and the surface receptor antibody at any time and for any period of time in the overall course of culturing (i.e., both IL-2 and the surface receptor antibody need only be present in the culturing medium at some time during the entire period of time the lymphocytes are cultured).

The culturing method of the present invention may also include culturing the lymphocytes in the presence of, in addition to IL-2 and a surface receptor antibody, a second lymphokine that enhances the LAK activity of the lymphocytes. Preferably, the second lymphokine is beta interleukin-1, gamma interferon, beta interferon or alpha interleukin-1. The second lymphokine may be a recombinant product or derived from another source.

As used throughout the specification and the appended claims, "cultured" or "culturing" shall mean the placing of cells in a medium containing, among other things including nutrients needed to sustain the life of the cultured cells, any specified added substances (e.g., IL-2). Cells are cultured "in the presence of" a specified substance when the medium in which such cells are maintained contains such specified substance. Culturing can take place in any vessel or apparatus in which the cells can be maintained exposed to the medium, including without limitation petri dishes, culture dishes, blood collection bags, roller bottles, flasks, test tubes, microtiter wells, hollow fiber cartridges or any other apparatus known in the art.

Methods of medical treatment are also disclosed in which cells cultured in accordance with the culturing methods of the present invention are introduced into the individual to be treated. The cells which are cultured can be obtained by leukopheresis, by venipuncture, from tumor tissues or from any other tissue or body fluid which is a source of lymphocytes. Another method of medical treatment is disclosed in which less than $4 \times 10^9$ lymphocytes are obtained from a lymphocyte source, cultured in the presence of IL-2 and an antibody to a lymphocyte surface receptor such that the lymphocytes develop LAK activity and increase in number to at least about $2 \times 10^{10}$ cells, preferably $2 \times 10^{11}$ cells. The resulting cells are then introduced into the individual to be treated. Preferably, the lymphocytes used for the methods of treatment are obtained from the individual to be treated.

DETAILED DESCRIPTION OF THE PREFERRED EMBODIMENTS

In the first culturing method of the present invention, lymphocytes are cultured with an antibody to a cell-surface receptor in the presence of IL-2. Preferably, the antibody is a monoclonal antibody to a CD3 receptor, i.e., an anti-CD3 antibody. The combined use of an antibody to the cell receptor in the presence of IL-2 induces a larger proliferation of cells (an average of 1,000-fold increase in cell number) over the course of up to 21 days with a substantial increase being noted on day 14. The lymphocytes can also be cultured in the presence of IL-2 with anti-CD3 and an additional lymphokine which causes an additional increase in LAK activity. Preferred additional lymphokines include beta interleukin-1 ($\beta$IL-1), alpha interleukin-1 (aIL-1), beta interferon ($\beta$IFN) and gamma interferon (gIFN). The additional lymphokine employed in practicing the invention can be a naturally-occurring lymphokine, a recombinant lymphokine, a lymphokine from any other source or a fragment or analog of a lymphokine, such fragment or analog having the same effect as a lymphokine.

Example 1

PBL were isolated from heparinized venous blood by centrifugation over Ficoll-Hypaque. Isolated cells were washed three times with phosphate buffered saline, counted and cultured in 16 mm wells (commercially available from Costar, Cambridge, Massachusetts, as No. 3424) at a density of $0.5 \times 10^6$ cells/ml in 2 ml tissue culture medium containing RPMI 1640 with 25 mM HEPES, 2 mM L-glutamine, 100 U/ml penicillin, 100 $\mu$g/ml streptomycin, 6% pooled human serum (hereinafter "TCM"). Cultures receiving IL-2 were supplemented with 1000 U/ml IL-2 (recombinant product from Cetus Corporation, California). Cultures treated with anti-CD3 were supplemented with 10 ng/ml of OKT3 monoclonal antibody (commercially available from Johnson & Johnson, Ortho Division, New Jersey) on the first day of culture. Cultures with and without OKT3 were initially seeded at a density of $0.5 \times 10^6$ cells/ml. After 48 hours and every 48 hours thereafter, the OKT3-supplemented cultures were diluted in fresh TCM plus IL2 without OKT3, to lower cell density to $0.1-0.2 \times 10^6$ cells/ml, Cultures not receiving OKT3 were also subcultured every 48 hours at a density of $0.1-0.2 \times 10^6$ cells/ml, Cells were carefully counted every 48 hours.

NK-resistant target was prepared from surgical specimens of melanoma metastases. Tumor specimens were washed in phosphate buffered saline (PBS), then minced on a glass petri dish in RPMI 1640 supplemented with 5% human serum. Necrotic tissue was removed and samples of the tumor were put in RPMI 1640 supplemented with 0.02 mg/ml of deoxyribonuclease, 0.01 mg/ml hyaluronidase and 1 mg/ml of collagenase. The tumor pieces were constantly stirred from 6 hours to 24 hours. The cell suspension was removed and centrifuged in 50 ml conical tubes (commercially available from Falcon, Becton Dickinson, California). The cell pellet was resuspended in 50 ml of TCM and further purified by centrifugation over FicollHypaque. The cells at the interface were harvested and washed three times in PBS, The cells were kept frozen in TCM supplemented with 20% serum and 10% dimethyl sulfoxide until they were thawed on the same day the assay for LAK activity was performed. Target cells were tested for NK sensitivity with fresh PBL and were shown to be NK-resistant prior to use in any assay for LAK activity.

Target tumor line K562 was maintained in culture in RPMI 1640 supplemented with 10% fetal bovine serum. Cells were seeded at $0.5 \times 10^6$/ml and aliquots were recultured in fresh media twice a week.

NK activity was measured as cytolytic activity against K562 targets. LAK activity was measured as cytolytic activity against NK-resistant targets, including HL60 and fresh tumor cells prepared as described above, To compare levels of LAK activity in long-term cultures with cells cultured for 5 days, and to eliminate, to the extent possible, variability introduced when the same target is tested on different days, lytic activities of long-term and short-term cultures were tested on the same day. That is, cells were taken from the same donor at two different times such that cells cultured for only 5 days were tested on the same day as those cells cultured for 14 (or more) days.

Cytolytic activity was measured according to the procedure for cell mediated lympholysis described by Rosenberg et al., N. Engl. J. Med. 313(23):1485 (1985), which is incorporated herein by reference. In summary, tumor and tumor line targets were labeled with 500 μCl of Na$^{51}$CrO$_4$ for one hour at 37° C. Cells were washed once in culture media, resuspended in culture media that did not contain IL-2 and allowed to remain at room temperature for 60 minutes which permits the spontaneous release of $^{51}$Cr. Cells were then washed twice, resuspended in fresh media, counted, and aliquoted at 500 targets/well in a 96-well V bottom plate on which the effectors had been previously aliquoted at set concentrations. The effector to target ratios ranged from 30:1 to 0.1:1. Plates were centrifuged at 500 rpms for 5 minutes and put in the incubator for 4 hours after which 150 μl of media was harvested from each well into a scintillation vial with 3 mils of scintillation fluid and radioactivity was counted in a liquid scintillation counter.

One lytic unit for tumor line K562 was defined as the number of effector cells needed to lyse 40% of the target cells. One lytic unit for all NK-resistant targets was defined as the number of cells needed to lyse 30% of the target cells.

Percent cytotoxicity was determined according to the formula:

$$\frac{(\text{experimental cpm}) - (\text{spontaneous cpm})}{(\text{maximal cpm}) - (\text{spontaneous cpm})} \times 100$$

Cell proliferation was determined by 3H-thymidine incorporation according to methods well known in the art. Cell number was determined by direct counting in a counting chamber or hemocytometer.

Figure 1:
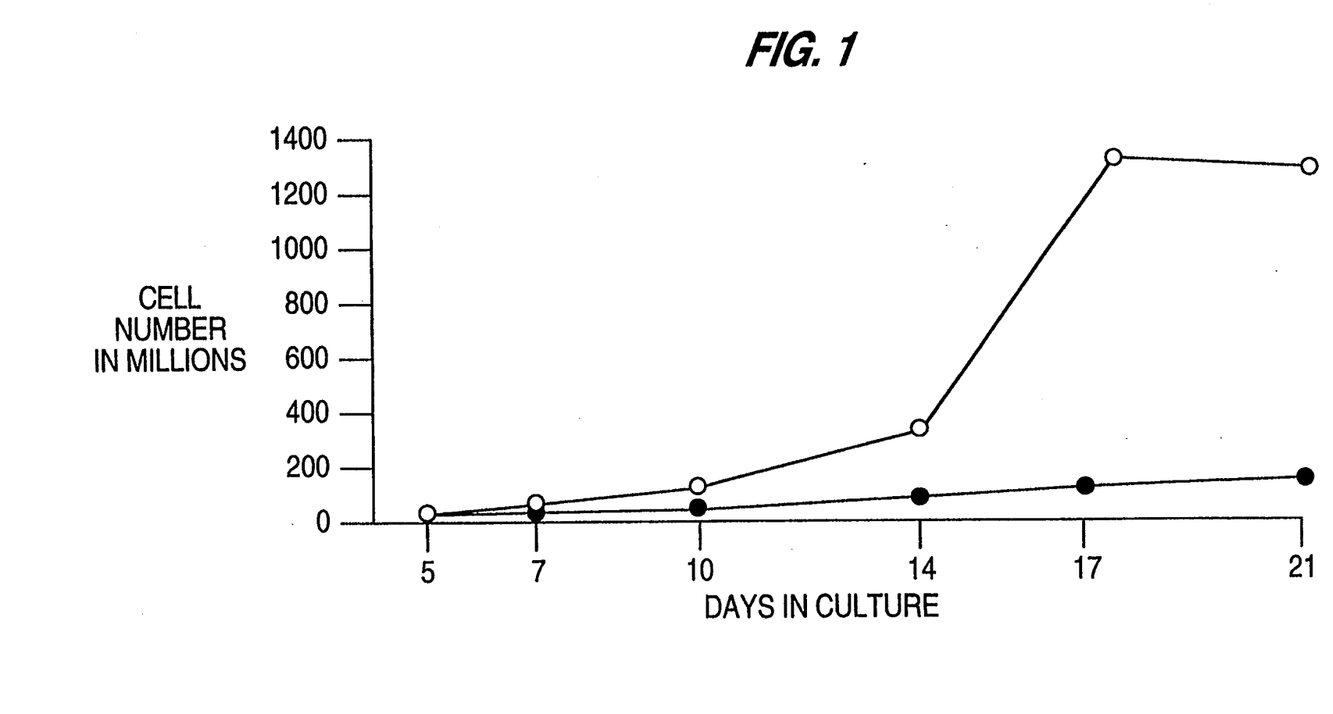
FIG. 1 Is a graph which shows the increase in the number of peripheral blood lymphocytes cultured with IL-2 alone and IL-2 plus anti-CD3.
Figure 2:
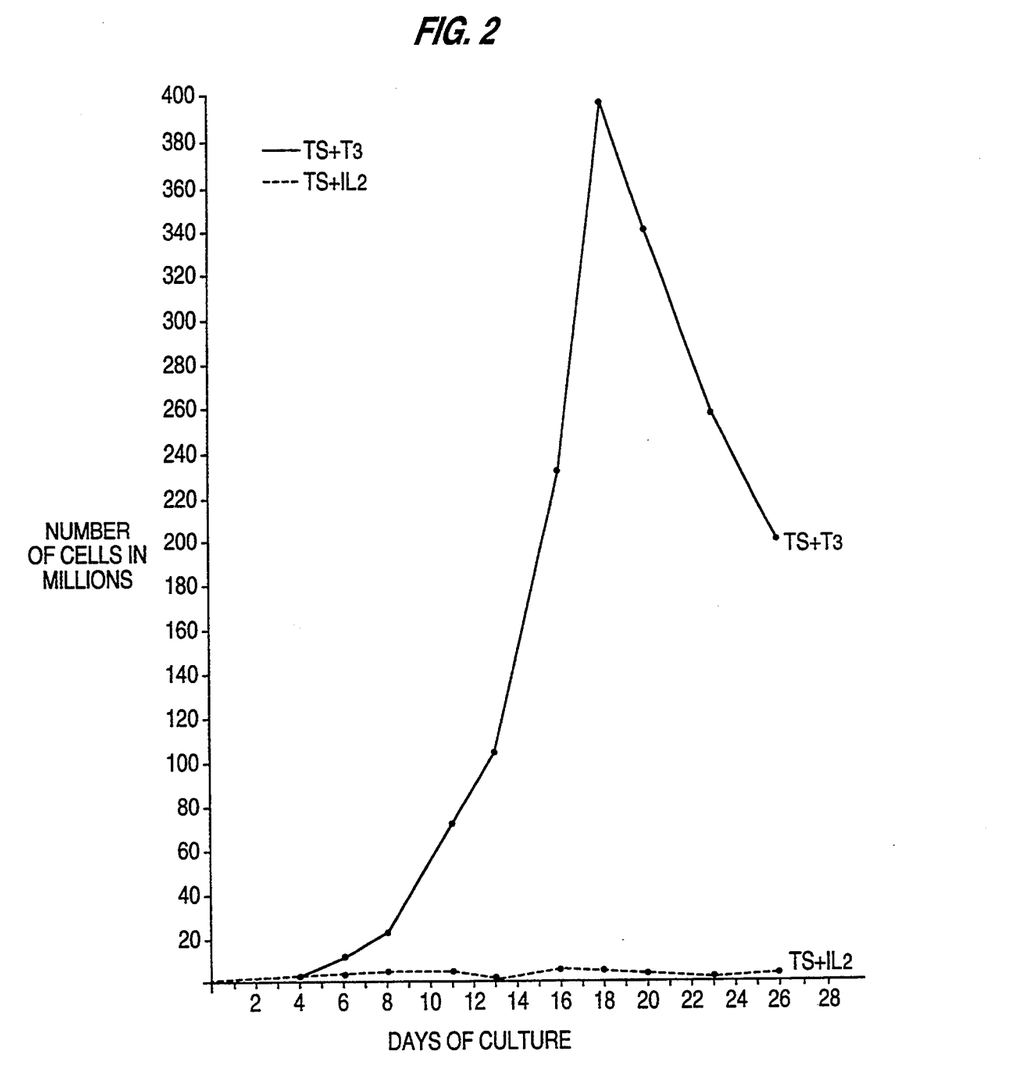
FIG. 2 Is a graph which shows the increase in the number of tumor infiltrating lymphocytes, from a tumor from a patient identified as "TS", cultured with IL-2 alone and IL-2 plus anti-CD3.
Figure 3:
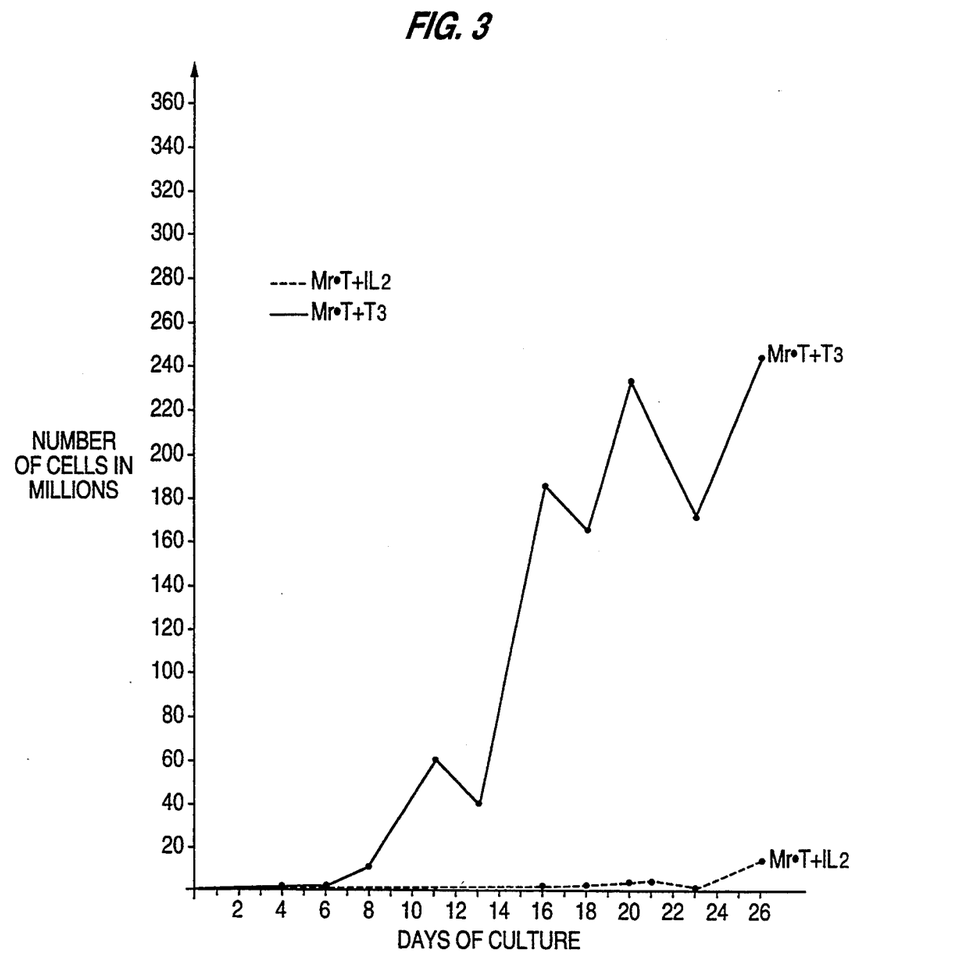
FIG. 3 is a graph which shows the increase in the number of tumor infiltrating lymphocytes, from a renal cell carcinoma (1), cultured with IL-2 alone and IL-2 plus anti-CD3.
Figure 4:
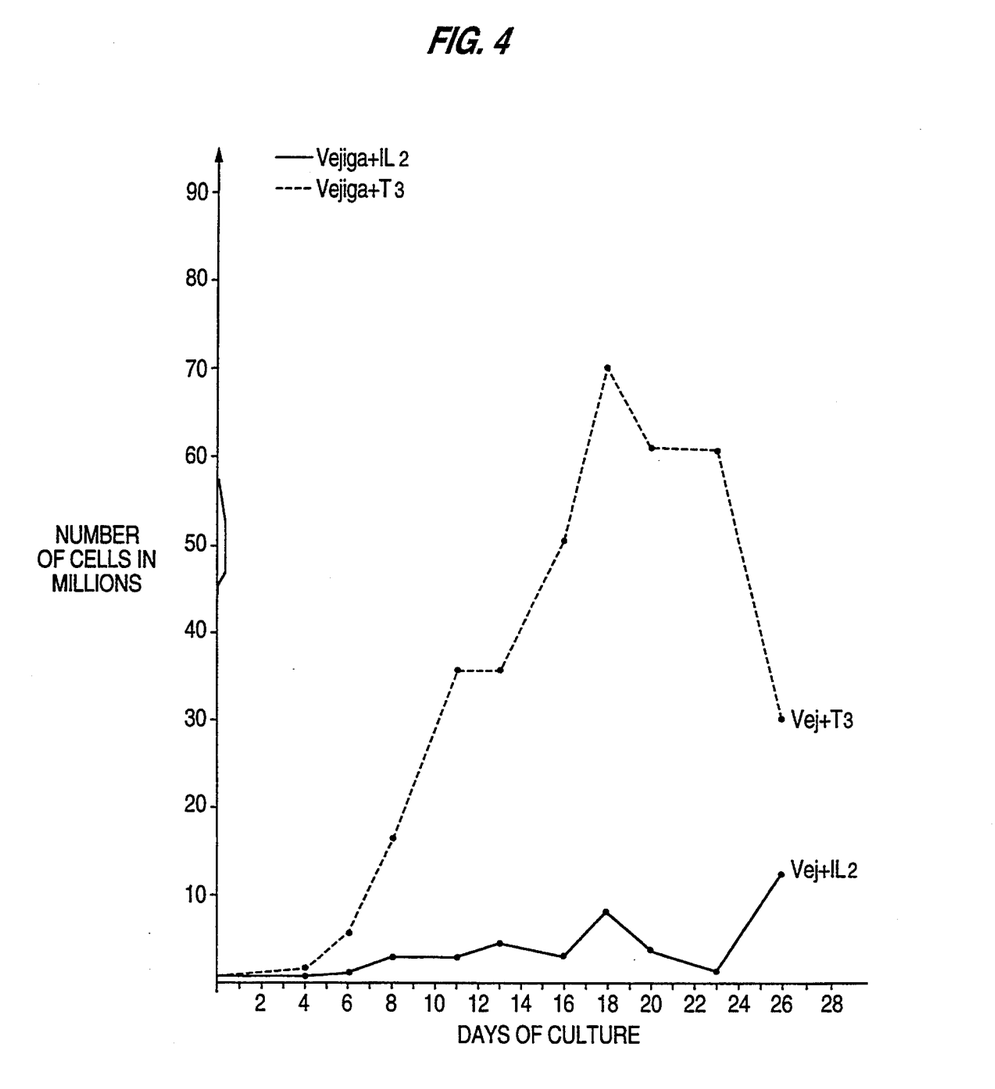
FIG. 4 is a graph which shows the increase in the number of tumor infiltrating lymphocytes, from a tumor from a bladder carcinoma, cultured with IL-2 alone and IL-2 plus anti-CD3.
Figure 5:
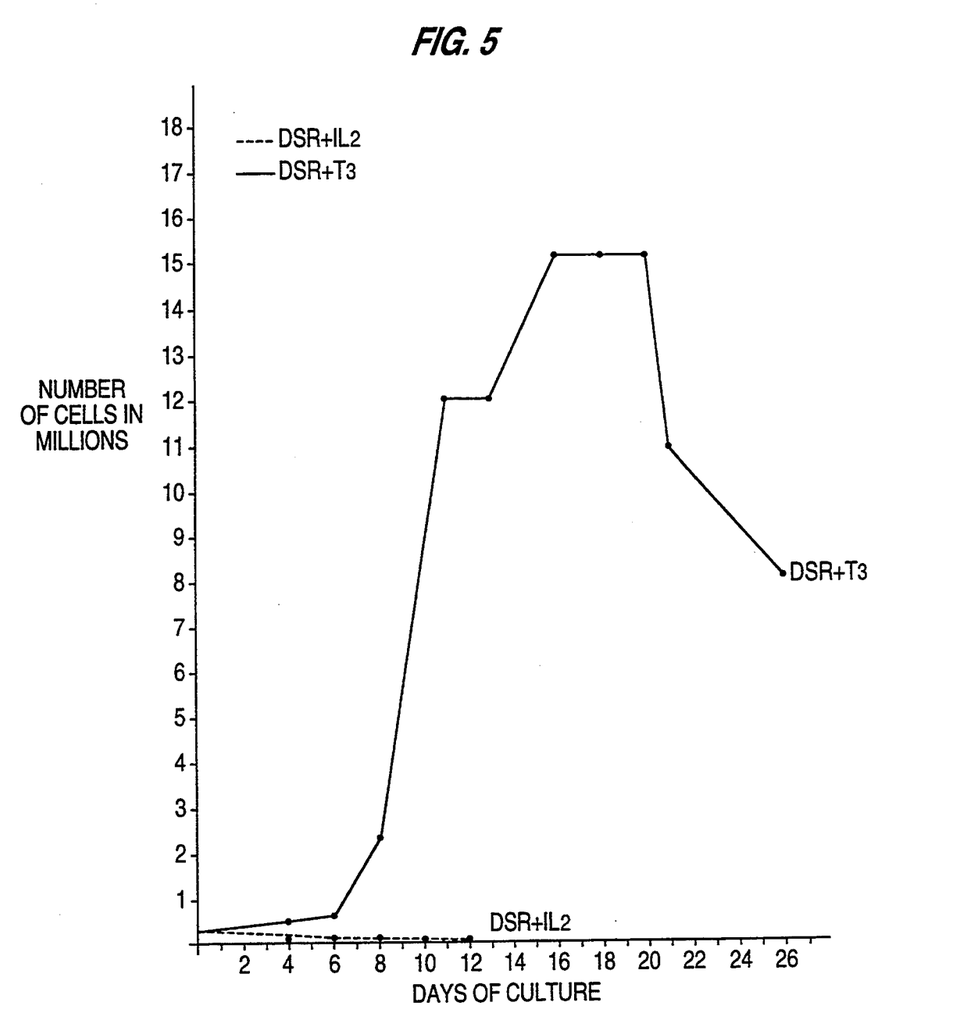
FIG. 5 is a graph which shows the increase in the number of tumor infiltrating lymphocytes, from a renal cell carcinoma (2), cultured with IL-2 alone and IL-2 plus anti-CD3.

FIG. 1 shows the expansion of cells cultured in IL-2 alone and IL-2 with anti-CD3. Cells cultured in IL-2 alone had a 123-fold increase in cell number by day 21. In contrast, cells cultured in IL-2 plus anti-CD3 showed an initial 324-fold increase on day 14 and a 1296-fold increase on day 21. The exhibited increase in cell number is sufficient to produce more than $2 \times 10^{10}$ or $2 \times 10^{11}$ cells from a single standard leukopheresis.

LAK and NK activities were tested in these cultures until day 14. Table 1 summarizes the activity data.

TABLE I

| Day | PHL + IL-2 | | | PBL + IL-2 + OKT3 | | |
|---|---|---|---|---|---|---|
| | 30:1[a] | 10:1 | 3:1 | 30:1 | 10:1 | 3:1 |
| | Target HL60 | | | | | |
| 3 | 50[b] | 43 | 6 | 52 | 47 | 26 |
| 5 | 51 | 30 | 14 | 16 | 10 | 8 |
| 7 | 64 | 38 | 14 | 10 | 3 | 2 |
| 12 | 40 | 35 | 22 | 28 | 17 | 8 |
| 14 | 22 | 22 | 4 | 56 | 32 | 12 |
| | Target K562 | | | | | |
| 3 | 48 | 36 | 14 | 64 | 58 | 38 |
| 5 | 60 | 49 | 27 | 54 | 38 | 15 |
| 7 | 89 | 63 | 36 | 7 | 2 | 1 |
| 12 | 73 | 56 | 46 | 67 | 40 | 18 |
| 14 | 53 | 49 | 23 | 55 | 34 | 11 |

[a] Effector: target ratio.
[b] % cytotoxicity. All standard deviations were < 100%.

Cells grown with IL-2 plus anti-CD3 showed a significant decrease in their ability to lyse the NK-resistant target HL60 on days 5 and 7, as well as a decreased ability to lyse the NK-sensitive target K562. At the same time, however, cell growth remained actively proliferating (see FIG. 1). On day 12, cells cultured with IL-2 plus anti-CD3 showed a significant increase in lytic activity compared to day 7.

Although the lytic activity per cell for cell cultures with IL-2 plus anti-CD3 is similar to the lytic activity per cell for cells cultured with IL-2 alone, the lyric activity per culture with IL-2 plus anti-CD3 is greater due to the substantial increase in cell numbers as compared to cultures with IL-2 alone.

PBL were collected and isolated as described above in Example 1. Cells were cultured for 12 days in IL-2 and OKT3 as described above in Example 1.

The cells were counted on day 12 of culture, Aliquots of $0.4 \times 10^6$ cells were distributed into new wells containing 2 ml TCM supplemented with 1000 U/ml IL-2 and either (a) 0.5 U/ml βIL-1 (recombinant product commercially available from Genzyme, Boston, Massachusetts); (b) 3 U/ml βIFN (recombinant product commercially available from Triton Corporation, Alameda, California); or (c) 100 U/ml gIFN (recombinant product commercially available from Biogen, Boston, Massachusetts). Cells were tested for LAK activity and 3H thymidine incorporation 48 hours later. LAK and NK activity were tested in parallel with control cells cultured in IL-2 alone or IL-2 plus anti-CD3.

LAK activity was measured as described in Example 1 above. Cell number was determined by direct counting in a hemocytometer.

Table 2 summarizes data relating to the effect of βIL-1, βIFN and gIFN on cells which were cultured in IL-2 and anti-CD3 for 12 days and were recultured for 48 hours in TCM containing IL-2 and one of these additional lymphokines,

TABLE 2

|  | LU/million cells[a] | LU/culture | LU/million cells | LU/culture |
|---|---|---|---|---|
| PBL + IL-2 | 2.9[b] | 200 | 1.7 | 117 |
| PBL + IL-2 + anti-CD3 | 3.3 | 1800 | 1.8 | 980 |
| PBL + IL-2 + anti-CD3 + 0.5 U/ml βIL-1 | 20.0 | 10700 | 1.5 | 827 |
| PBL + IL-2 + anti-CD3 + 3 U/Ml βIFN | 12.5 | 6700 | 0.25 | 135 |
| PBL + IL-2 + anti-CD3 + 100 U/ml gIFN | 10.0 | 5400 | 0.23 | 126 |

[a] Tumor cells were thawed the day of the assay. Wells were seeded at effector-to-target ratios ranging from 30:1 to 0.1:1.
[b] Lytic units x $10^3$ $^{1.3}$ Cells cultured in TCM containing IL-2 plus anti-CD3 showed increased LAK activity after culture in the presence of either βIL-1, βIFN or gIFN. βIL-1 induced the highest increase in LAK activity on a per cell basis ($20 \times 10^3$ LU/million cells) compared to cells cultured in IL-2 alone ($2.9 \times 10^3$ LU/million cells) or IL-2 plus anti-CD3 ($3.3 \times 10^3$ LU/million cells). βIFN induced an increase to $12.5 \times 10^3$ LU/million cells while gIFN induced an increase to $10 \times 10^3$ LU/million cells. This increase in LAK activity on a per-cell basis together with the high number of cells achieved by stimulating the cells with anti-CD3 plus IL-2, results in increases in lyric units/culture ranging from 27-fold when cultured with gIFN to 53-fold when cultured with βIL-1 as compared with cells cultured only in IL-2 alone.

The data in Table 2 also demonstrates the proliferative effect of IL-2 and anti-CD3 without additional lymphokines. Although cells cultured in medium containing IL-2 plus anti-CD3 for 14 days (line 2) had approximately the same lytic activity per million cells as cells grown in IL-2 alone (line 1), the total lytic activity of these cultures was increased approximately 9-fold due to the significant increase in cell numbers resulting from the culture method of the present invention. On occasion these cultures had slightly less LAK and NK activity on a per-cell basis.

Table 3 shows the 3H-thymidine incorporation of the cultures described above, suggesting that the additional lymphokines do not induce additional proliferation of the cultured cells.

TABLE 3

|  |  | cpm x $10^{-3}$ [a] |
|---|---|---|
| 1 | PBL + IL-2 | 97 |
| 2 | PBL + IL-2 + OKT3 | 20 |
| 2A | PBL + IL-2[a] + OKT3 + βIL-1 | 21 |
| 2B | PBL + IL-2[a] + OKT3 + βIFN | 16 |
| 2B | PBL + IL-2 + OKT3 + gIFN | 22 |

[a] Cells from culture number 2 were taken on day 12 and recultured in separate wells containing 1000 U/ml IL-2 plus either 0.5 U/ml βIL-1. 3 U/ml βIFN or 100 U/ml gIFN. $^3$H-thymidine incorporation was then assayed on day 14.

Since none of the three lymphokines added on day 12 induced any detectable proliferative response on day 14 above that produced by IL-2 plus anti-CD3, this suggests that the increase in lytic activity as shown in Table 2 is caused by either (a) LAK cells becoming more active killers on an individual cell basis, or (b) the induction of LAK activity by the additional lymphokines.

aIL-1 at a concentration of 25–75 U/ml was also shown to stimulate an increase in antitumor activity.

Example 3

Tumor-infiltrating lymphocytes ("TIL" cells; TIL cells are described in further detail in Rosenberg et al.., Science 233:1318 (1986), which is incorporated herein by reference) were isolated from tumor tissue of various kinds excised from patients. Patient tumor tissues included neuroblastoma, three renal cell carcinomas, bladder carcinoma and tumor from a patient identified as "TS" (the character of which was unknown). The tumor tissues were minced and TIL cells were isolated according to the procedure described in Example 1 above for isolation of fresh tumor cells to be used as NK-resistant targets. Isolated TIL cells were frozen until the moment they were put in culture.

Isolated TIL cells were cultured with IL-2 and IL-2 plus anti-CD3 as described above in Example 1. LAK activity was measured as described above in Example 1. Cell proliferation was determined by 3H-thymidine incorporation according to methods well known in the art. Cell number was determined by direct counting in a counting chamber or hemocytometer.

Data relating to the proliferative response of TIL cells from a tumor from a patient identified as "TS", a renal cell carcinoma (1), a bladder carcinoma and a renal cell carcinoma (2), which were all cultured over the course of 26 days in IL-2 alone and IL-2 plus anti-CD3, is shown in FIGS. 2, 3, 4 and 5, respectively. In each case addition of anti-CD3 to the culture medium stimulated an approximate 2–100 fold increase in cell number depending on the type of cell cultured and the time at which the culture was counted. TIL cells from the TS tumor and renal carcinoma (1) showed the greatest proliferative response to anti-CD3. As seen with the PBL cultures in Example 1 above, the exhibited increase in cell number during culturing of the TIL cells is sufficient to produce more than $2 \times 10^{10}$ or $2 \times 10^{11}$ cells from a single standard leukopheresis.

LAK activity was measured against HL60, Daudi and the following NK-resistant fresh tumor targets: neuroblastoma (NK-resistant target A), renal cell carcinoma (NK-resistant target B) and lymphoblastoid (B-cell) transformed with virus (NK-resistant target C). LAK activity data for TIL cells cultured with IL-2 alone and IL-2 plus anti-CD3 is summarized in Tables 4 and 5, respectively.

TABLE 4

| TIL effecter from: | day | ratio[a] | NK-resistant target | | | | |
|---|---|---|---|---|---|---|---|
| | | | HL60 | Daudi | A | B | C |
| neuroblastoma | 10 | 30:1 | −5.3[b,c] | | −6.9 | 25.0 | −4.1 |
| | | 10:1 | −3.5 | | −0.4 | 4.6 | −1.2 |
| | | 3:1 | −4.2 | | −1.9 | 4.6 | −3.4 |
| | | 1:1 | −3.1 | | −6.0 | −2.8 | 1.3 |
| | | 0.3:1 | −3.1 | | 0.1 | −8.3 | 0.3 |
| | | 0.1:1 | −4.5 | | −3.5 | −4.3 | 0.1 |
| renal cell carcinoma (1) | 14 | 30:1 | | | 2.5 | | |
| | | 10:1 | | | 3.7 | | |
| | | 3:1 | | | −5.1 | | |
| | | 1:1 | | | −7.9 | | |
| | | 0.3:1 | | | −4.4 | | |
| | | 0.1:1 | | | 1.0 | | |
| | 21 | 30:1 | 15.4 | | | 52.6 | 2.9 |
| | | 10:1 | 5.8 | | | 37.9 | 1.8 |
| | | 3:1 | 0.5 | | | 17.9 | 0.6 |
| | | 1:1 | −1.4 | | | 13.4 | 5.1 |
| | | 0.3:1 | −2.4 | | | 0.3 | -0.4 |
| | | 0.1:1 | −1.5 | | | −0.7 | 0.6 |
| bladder carcinoma | 14 | 30:1 | | 53.1 | | 54.8 | 5.3 |
| | | 10:1 | | 51.1 | | 52.8 | 7.9 |
| | | 3:1 | | 26.6 | | 29.2 | 2.3 |
| | | 1:1 | | 15.4 | | 11.4 | 3.5 |
| | | 0.3:1 | | 7.6 | | 7.9 | 1.8 |
| | | 0.1:1 | | 8.0 | | 6.0 | 0.9 |
| | 19 | 30:1 | 25.7 | | | 66.3 | −1.8 |
| | | 10:1 | 19.0 | | | 42.5 | −5.0 |
| | | 3:1 | 6.7 | | | 29.4 | 8.6 |
| | | 1:1 | 1.9 | | | 16.7 | −1.2 |
| | | 0.3:1 | 0.3 | | | 3.2 | −8.7 |
| | | 0.1:1 | −0.3 | | | 13.5 | −4.4 |
| tumor from patient TS | 14 | 30:1 | | 65.7 | | 66.1 | 19.9 |
| | | 10:1 | | 101.1 | | 54.9 | 30.7 |
| | | 3:1 | | 56.9 | | 24.7 | 13.2 |
| | | 1:1 | | 32.3 | | 19.0 | 4.1 |
| | | 0.3:1 | | 6.5 | | 7.7 | 1.9 |
| | | 0.1:1 | | 4.9 | | 1.6 | 0.4 |
| | 19 | 30:1 | 38.2 | | | 52.3 | 14.3 |
| | | 10:1 | 44.8 | | | 53.8 | 14.5 |
| | | 3:1 | 23.3 | | | 42.9 | 5.2 |
| | | 1:1 | 13.1 | | | 27.3 | −1.4 |
| | | 0.3:1 | 5.0 | | | 0.5 | −3.0 |
| | | 0.1:1 | 1.3 | | | 13.2 | −6.0 |

[a] Effector to target ratio
[b] Percent cytotoxicity
[c] Negative value indicates that the experimental counts were less than background.

TABLE 5

| TIL effecter from: | day | ratio[a] | NK-resistant target | | | | |
|---|---|---|---|---|---|---|---|
| | | | HL60 | Daudi | A | B | C |
| neuroblastoma | 10 | 30:1 | 4.0[b,c] | | 0.6 | 18.4 | 9.4 |
| | | 10:1 | 2.8 | | 18.3 | 4.7 | 5.6 |
| | | 3:1 | −2.7 | | 6.6 | −0.2 | 2.5 |
| | | 1:1 | −5.1 | 2.9 | 12.1 | 1.1 | |
| | | 0.3:1 | −2.8 | | −5.1 | −3.2 | 3.5 |
| | | 0.1:1 | −3.7 | | −1.1 | −0.5 | 2.8 |
| renal cell carcinoma (1) | 14 | 30:1 | | 3.6 | | 6.8 | 1.6 |
| | | 10:1 | | 4.5 | | 7.7 | −1.8 |
| | | 3:1 | | 2.0 | | −1.4 | −2.6 |
| | | 1:1 | | 1.7 | | 6.2 | −1.1 |
| | | 0.3:1 | | 0.7 | | 2.3 | −1.3 |
| | | 0.1:1 | | 2.0 | | −3.6 | 0.8 |
| | 19 | 30:1 | 28.7 | | | 27.1 | 13.3 |
| | | 10:1 | 10.1 | | | 20.4 | −9.8 |
| | | 3:1 | 8.6 | | | 15.4 | −4.5 |
| | | 1:1 | 5.0 | | | 8.5 | 8.8 |
| | | 0.3:1 | 2.3 | | | 1.7 | 1.4 |
| | | 0.1:1 | 1.2 | | | 4.8 | −1.2 |
| | 21 | 30:1 | 16.3 | | 19.3 | 33.0 | 2.5 |
| | | 10:1 | 7.2 | | 1.6 | 17.8 | 2.7 |
| | | 3:1 | 3.5 | | −2.6 | 3.5 | −0.6 |
| | | 1:1 | 2.5 | | 2.1 | −0.7 | 2.7 |
| | | 0.3:1 | 0.2 | | 0.2 | 3.6 | 4.4 |
| | | 0.1:1 | 0.4 | | −0.4 | −2.1 | 2.1 |
| renal cell carcinoma (2) | 19 | 30:1 | 1.2 | | | 4.1 | 9.3 |
| | | 10:1 | 2.0 | | | 26.2 | 0.4 |
| | | 3:1 | 1.5 | | | 14.4 | −5.6 |

TABLE 5-continued

| TIL effecter from: | day | ratio[a] | NK-resistant target | | | | |
|---|---|---|---|---|---|---|---|
| | | | HL60 | Daudi | A | B | C |
| | | 1:1 | 1.2 | | | 13.5 | −0.6 |
| | | 0.3:1 | 0.6 | | | 15.0 | −3.6 |
| | | 0.1:1 | 0.4 | | | 13.2 | −3.2 |
| renal cell carcinoma (3) | 14 | 30:1 | | 31.4 | | 16.1 | 13.5 |
| | | 10:1 | | 23.5 | | 18.1 | 8.5 |
| | | 3:1 | | 6.8 | | 5.0 | 5.6 |
| | | 1:1 | | 4.2 | | −0.8 | 0.8 |
| | | 0.3:1 | | 2.9 | | 0.3 | −0.7 |
| | | 0.1:1 | | 0.8 | | −0.7 | −1.6 |
| | 19 | 30:1 | 0.9 | | | 3.1 | 1.8 |
| | | 10:1 | −0.1 | | | 10.4 | 1.8 |
| | | 3:1 | −0.7 | | | 18.2 | −12.9 |
| | | 1:1 | 1.0 | | | 16.9 | −3.2 |
| | | 0.3:1 | 0.7 | | | 12.5 | 0.2 |
| | | 0.1:1 | −0.1 | | | 5.7 | −2.8 |
| bladder carcinoma | 14 | 30:1 | | 26.0 | | 26.6 | 5.1 |
| | | 10:1 | | 25.1 | | 22.0 | 4.9 |
| | | 3:1 | | 12.4 | | 14.2 | 0.1 |
| | | 1:1 | | 3.0 | | 8.3 | 1.1 |
| | | 0.3:1 | | 1.6 | | 2.7 | −1.3 |
| | | 0.1:1 | | 1.2 | | 5.3 | −0.3 |
| | 19 | 30:1 | 19.3 | | | 37.7 | 0.6 |
| | | 10:1 | 11.4 | | | 35.3 | −6.2 |
| | | 3:1 | 2.8 | | | 3.0 | −6.2 |
| | | 1:1 | 0.1 | | | 21.1 | 3.6 |
| | | 0.3:1 | 0.5 | | | 16.7 | −4.0 |
| | | 0.1:1 | 0.0 | | | 14.8 | −2.4 |
| tumor from patient TS | 14 | 30:1 | | 33.0 | | 40.5 | 7.0 |
| | | 10:1 | | 40.5 | | 29.5 | 7.7 |
| | | 3:1 | | 15.9 | | 26.7 | 5.4 |
| | | 1:1 | | 11.5 | | 7.6 | 3.5 |
| | | 0.3:1 | | 2.6 | | 3.1 | −0.1 |
| | | 0.1:1 | | 2.4 | | 4.9 | 1.8 |
| tumor from patient TS | 19 | 30:1 | 46.0 | | | 66.8 | 1.8 |
| | | 10:1 | 75.3 | | | 52.9 | 5.7 |
| | | 3:1 | 15.9 | | | 35.7 | −0.6 |
| | | 1:1 | 7.3 | | | 8.6 | −12.0 |
| | | 0.3:1 | 1.8 | | | 15.7 | −6.2 |
| | | 0.1:1 | 1.0 | | | 3.7 | −8.8 |

[a] Effector to target ratio
[b] Percent cytotoxicity
[c] Negative value indicates that the experimental counts were less than background.

Each type of cultured TIL cell exhibited some significant cytotoxic effect when cultured with IL-2 alone and IL-2 plus anti-CD3. Peak effect was apparently dependant upon certain effector/target pairs and effector:target ratios. Due to the significant increase in cell number caused by culture with anti-CD3 (see FIGS. 2–5), TIL cells cultured with anti-CD3 appear to exhibit a greater degree of cytotoxicity per culture than TIL cells cultured without anti-CD3.

Example 4

PBLs cultured with IL-2 plus anti-CD3 were administered to an Acquired Immunodeficieny Syndrome (AIDS) patient to determine whether such cells would cause a toxic reaction or other adverse side effects. PBLs were collected from the patient's twin brother and cultured as described above in Example 1. The resulting LAK cells were suspended in phosphate buffered saline supplemented with 5% human serum albumin and 375 U/ml IL-2. The resulting suspensions were then introduced into the each patient intravenously such that no more than 1010 cells were infused in a period of 30 minutes.

Before treatment with LAK cells, uncultured lymphocytes from the patient's twin were administered. The LAK cells were administered to the patient in two courses of treatment ($1.4 \times 10^{10}$ and $5 \times 10^{10}$) separated by a period of approximately one month. $9.6 \times 10^{10}$ cells were actually recovered from culturing for the second course, but only $5 \times 10^{10}$ cells were administered to the patient. The first course of cells was administered with no additional systemic injection of IL-2. The second course of cells was administered with 1000–3000 U/m² IL-2 and followed up with 1000–3000 U/m² IL-2 each day for at least 4 days thereafter.

The patient showed no toxic or other adverse side effects from the cell therapy, other than some of those normally associated with the Rosenberg treatment protocol cited previously.

From the foregoing, it will be obvious to those skilled in the art that various modifications in the above-described methods can be made without departing from the spirit and scope of the invention. Accordingly, the invention may be embodied in other specific forms without departing from the spirit or essential characteristics thereof. Present embodiments and examples, therefore, are to be considered in all respects as illustrative and not restrictive, the scope of the invention being indicated by the appended claims rather than by the foregoing, and all changes which come within the meaning and range of equivalency of the claims are therefore intended to be embraced therein.

We claim:

1. A method of developing LAK activity in a population of cultured lymphocytes, said method comprising:
   (a) culturing said lymphocytes in a medium comprising IL-2 and an anti-CD3 antibody, in combination, for at least about 48 hours;

(b) removing said lymphocytes from said medium comprising IL-2 and an anti-CD3 antibody; and (c) culturing said lymphocytes in a medium comprising IL-2 without any additional anti-CD3 antibody, whereby LAK activity in said lymphocytes is developed.

2. The method of claim 1 wherein said lymphocytes increase in number from about $4 \times 10^9$ cells to at least about $2 \times 10^{10}$ cells.

3. The method of claim 1 wherein said lymphocytes maintain at least a portion of said LAK activity during at least the first seven days of culturing.

4. The method of claim 1 wherein said lymphocytes are obtained from peripheral blood.

5. The method of claim 1 wherein said lymphocytes are tumor infiltrating lymphocytes.

6. The method of claim 1 wherein said IL-2 is recombinant IL-2.

7. The method of claim 44 wherein in step (c), said medium further comprises a lymphokine, in addition to said IL-2, that enhances said LAK activity of said lymphocytes, said lymphokine being selected from the group consisting of $\alpha$IL-1, $\beta$IL-1, $\beta$-IFN and $\gamma$-IFN.

8. The method of claim 7 wherein said additional lymphokine is a recombinant lymphokine.

* * * * *